(12) United States Patent
Pagan

(10) Patent No.: US 8,534,288 B2
(45) Date of Patent: Sep. 17, 2013

(54) DETECTORS

(75) Inventor: Eric Pagan, Hythe (GB)

(73) Assignee: Smiths Group PLC, London (GB)

( * ) Notice: Subject to any disclaimer, the term of this patent is extended or adjusted under 35 U.S.C. 154(b) by 1068 days.

(21) Appl. No.: 12/308,568

(22) PCT Filed: Jun. 26, 2007

(86) PCT No.: PCT/GB2007/002383
§ 371 (c)(1),
(2), (4) Date: Dec. 18, 2008

(87) PCT Pub. No.: WO2008/003928
PCT Pub. Date: Jan. 10, 2008

(65) Prior Publication Data
US 2010/0065063 A1 Mar. 18, 2010

(30) Foreign Application Priority Data
Jul. 4, 2006 (GB) .................................. 0613213.8

(51) Int. Cl.
*A61M 16/20* (2006.01)
*G01N 21/78* (2006.01)
*A61B 5/097* (2006.01)

(52) U.S. Cl.
USPC ...................................... 128/207.16; 600/532

(58) Field of Classification Search
None
See application file for complete search history.

(56) References Cited

U.S. PATENT DOCUMENTS

| 5,005,572 | A | 4/1991 | Raemer |
| 2003/0109793 | A1 | 6/2003 | Ratner |
| 2004/0065329 | A1 | 4/2004 | Geist |

FOREIGN PATENT DOCUMENTS

| EP | 0 503 511 | 9/1992 |
| GB | 2218515 | 11/1989 |
| GB | 2405100 | 2/2005 |
| WO | 89/07956 | 9/1989 |
| WO | 95/11716 | 5/1995 |
| WO | 97/14464 | 4/1997 |

*Primary Examiner* — Shanon A Foley
(74) *Attorney, Agent, or Firm* — Louis Woo

(57) ABSTRACT

A respiratory valve assembly (1), such as in a manual resuscitator, has a carbon dioxide color change indicator element (52) in a disc shape housing (50) arranged to clip onto a grove (59) on the valve assembly. Expiratory and inspiratory gas is supplied to the housing via two flexible tubes (60) and (61) extending side-by-side from the valve assembly (1) to the indicator housing (50) so that the indicator can be undipped from the valve and repositioned if desired.

10 Claims, 1 Drawing Sheet

DETECTORS

This invention relates to detectors of the kind including a gas detector element in a housing arranged to provide a visual indication of change in level of a selected gas.

The invention is more particularly concerned with detectors for detecting carbon dioxide.

One of the major problems associated with the use of an endotracheal tube is that of ensuring that the patient end of the tube is correctly located in the trachea and not in the oesophagus. There are various ways in which correct intubation can be detected. The usual way is to connect the machine end of the tube to a capnograph, which is responsive to the levels of carbon dioxide. When the tube is correctly inserted, the level of carbon dioxide detected rises and falls with the patient's breathing. By detecting this alternating level of carbon dioxide, correct intubation is indicated. If the tube is incorrectly inserted, in the oesophagus, any carbon dioxide produced by the digestive system will be at a relatively steady level. Capnographs can produce a reliable indication of correct intubation but the equipment is relatively bulky and expensive so it is only available in well-equipped surgical operating theatres.

An alternative device can be used to detect carbon dioxide, which includes a chemical colour-change or colorimetric indicator, such as described in, for example, WO96/24054, EP509998, U.S. Pat. No. 5,005,572, U.S. Pat. No. 4,879,999, EP257916, U.S. Pat. No. 4,691,701, U.S. Pat. No. 4,790,327, WO89/07956, GB2218515, U.S. Pat. No. 6,378,522 and U.S. Pat. No. 4,728,499. This form of device usually comprises a paper or some other substrate that is impregnated or coated with the chemical including a pH-sensitive indicator dye, the substrate preferably being provided in some form of transparent connector attached to the machine end of the tube. Such indicators can be of low cost and can provide a clear indication that the tube has been correctly inserted. If the indicator fails to change colour, the clinician knows immediately that the tube has been incorrectly inserted. Preferably, the indicator is arranged to change back and forth between two different colours as it is exposed to expiratory (high carbon dioxide) gas and to fresh (low carbon dioxide) gas, such as inspiratory gas.

It can be difficult to locate the indicator in a position where it has maximum visibility and where it will also be exposed to both expiratory gas and to fresh gas flow so that the indicator is exposed to alternate high and low levels of carbon dioxide to produce the alternating colour change.

According to one aspect of the present invention there is provided a gas detector of the above-specified kind, characterised in that the detector includes a first arrangement for supplying a first gas to the housing so that the element is exposed to the first gas, and a second arrangement for supplying a second gas to the housing so that the element is exposed to the second gas, that the first and second arrangements are arranged such that the concentration of the first and second gas to which the element is exposed varies alternately with time, and that at least one of the first or second supplying arrangements includes a flexible tube opening at one end into the housing.

The gas detector element preferably includes a colour change element. The gas detector element is preferably responsive to carbon dioxide levels. Both the first and second supplying arrangements may include respective flexible tubes. The two tubes preferably extend side-by-side and open into the housing at one end. The other end of the or each tube may open into a respiratory valve assembly. Alternatively, one of the supplying arrangements may be a flexible tube and the other of the supplying arrangements may be an opening into the housing. The housing is preferably enclosed and has a transparent portion through which the element can be viewed. The housing may be arranged to clip onto another component, such as a respiratory valve assembly. The housing is preferably disc shape.

According to another aspect of the present invention there is provided a respiratory valve assembly including a gas detector according to the above one aspect of the present invention.

A respirator valve assembly including a gas detector according to the present invention will now be described, by way of example, with reference to the accompanying drawings, in which.

Figure 1:
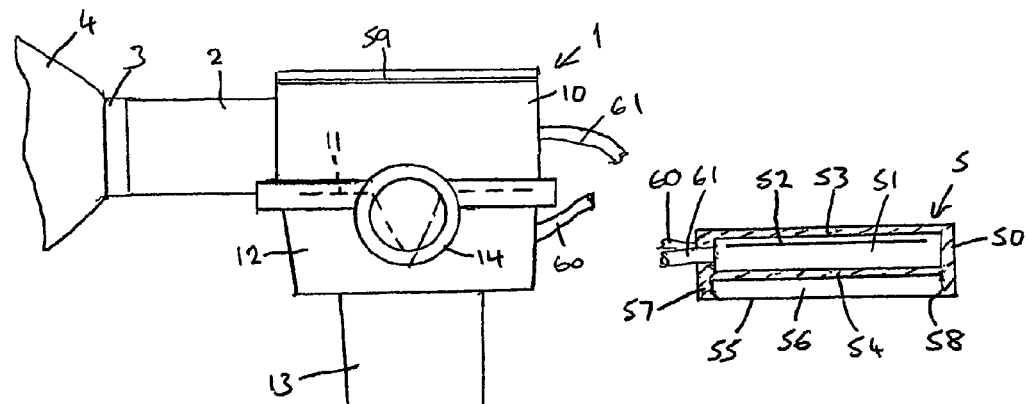
FIG. 1 is a side, partly-sectional elevation view of the assembly.
Figure 2:
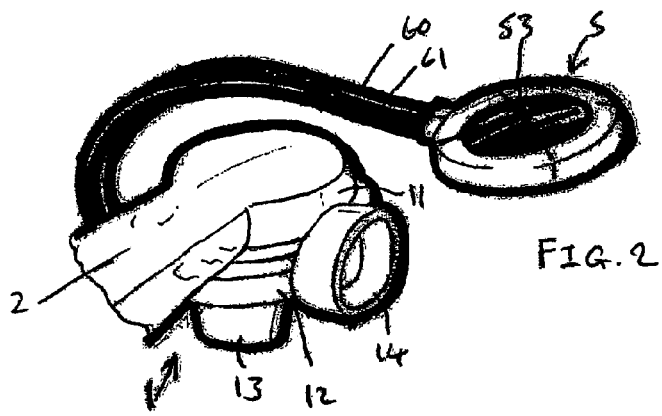
FIG. 2 is a perspective view of the assembly.

With reference to FIGS. 1 and 2, the assembly comprises a valve 1 with an inlet 2 connected with the outlet 3 of a resilient manual resuscitator squeeze bag 4. The assembly also includes a carbon dioxide gas detector 5 connected with the valve 1.

The valve 1 may be of a conventional kind having an upper chamber 10 with a flexible valve element 11 separating it from a lower chamber 12 to which a male tapered outlet coupling 13 is attached by a swivel connection. The coupling 13 is adapted to connect with a face mask or tracheal tube connection. The valve 1 also has an exhaust port 14 opening into the lower chamber 12. Operation of the valve is conventional so will not be described in detail here. Briefly, when the bag 4 is squeezed, air passes through the valve element 11 to the outlet coupling 13 for supplying air to the patient. The valve element 11 isolates the exhaust port 14 during the inspiratory phase, while air flows to the outlet coupling 13. When the bag 4 is released, the patient exhales and the expiratory gas flows from the outlet coupling 13 into the lower chamber 12 and out of the exhaust port 14 to atmosphere.

The gas detector 5 comprises a disc-shape transparent plastics housing 50 of circular section with a cylindrical internal cavity 51. An indicator disc 52 of a conventional colorimetric material is mounted in the housing 50 so that it is exposed to gas in the cavity 51 and so that it is visible through an upper circular window 53, or through both the upper and a lower window 54. The lower face 55 of the housing 50 has a shallow recess 56 with a peripheral, downwardly-extending rim 57 having an inwardly-directed lip 58 arranged to engage as a snap fit a groove 59 around the upper surface of the valve 1. In this way, the detector housing 50 can be clipped to the valve 1 or released from it as desired.

Two flexible tubes 60 and 61 open at one end into the cavity 51 in the housing 50 and connect the detector housing 50 with the valve 1. The tubes 60 and 61 extend side-by-side and are preferably joined with one another along most of their length. The opposite end of one tube 60 opens into the lower chamber 12 or some other part of the valve 1 where it will be exposed to expiratory breath from the patient. The opposite end of the other tube 61 opens into the upper chamber 10 or some other part of the valve where it will be exposed to inspiratory gas supplied to the patient.

When air is delivered to the patient by squeezing the bag 4, a small proportion of this air, which is relatively low in carbon dioxide, flows along the tube 61 to the cavity 51 in the housing 50. The indicator disc 52 is, therefore, exposed to a low level of carbon dioxide so has a colour that is indicative of this. When the bag 4 is released and the patient exhales, a portion of this expiratory gas flows along tube 60 to the cavity 51 in the housing 50 flushing out the air present in the cavity. This expiratory gas has a relatively high level of carbon dioxide so the indicator disc 52 turns a different colour to indicate the higher carbon dioxide level. When the bag 4 is squeezed again, the gas in the cavity 51 is flushed out and replaced by inspiratory gas so the indicator disc 52 changes colour again back to its original colour. As the patient is repeatedly ventilated, the indicator disc 52 changes colour back and forth.

If the respirator valve assembly is used with an endotracheal tube and if that tube is incorrectly inserted, in the oesophagus instead of the trachea, expiratory gas will not be provided by the patient's respiratory system so only low levels of carbon dioxide will flow to the detector 50. The result of this will be that the indicator disc 52 remains at a constant, low-$CO_2$ colour so that it is readily apparent to the user that the tube has been incorrectly placed. Similarly, when used with a face mask, a constant, low-$CO_2$ colour will be produced if the patient has died and no respiratory gas exchange is occurring in the lungs.

Connecting the detector 50 to the source of expiratory gas by a flexible tube 60 in the manner described enables the detector to receive the necessary gas whilst it can be positioned remote from the gas source in a position where it is most easily visible to the user. The detector could be clipped onto the top of the valve 1 or it could be placed on a convenient surface. The detector could have an adhesive rear surface to enable it to be secured to such a surface.

Figure 3:
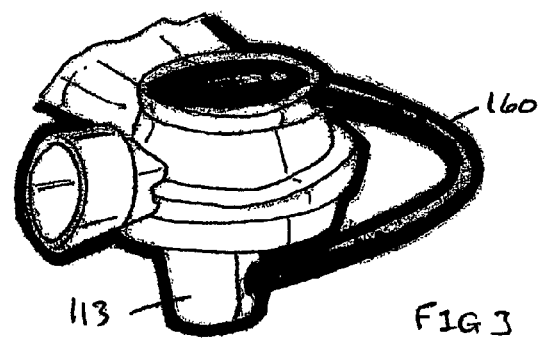
FIG. 3 is a perspective view of an alternative assembly.

It is not essential for the detector to be connected with two tubes providing there is at least a tube communicating with a source of expiratory breath. Where only one tube is used, the detector housing could have a small bleed hole to enable expiratory gas to escape and atmospheric gas to enter between the expiratory gas supply phases of respiration. FIG. 3 shows an arrangement having just one tube 160. In this arrangement the tube 160 connects to the outlet coupling 113. The detector housing could have an aperture (not shown) arranged to communicate with an aperture (not shown) in the valve housing opening into the upper chamber exposed to inspiratory gas. The detector would be clipped onto the valve housing over the aperture so that the inspiratory gas flows into the detector to flush out the expiratory gas between the expiratory phases. In such an arrangement it can be seen that the expiratory gas enters the detector via a tube and the inspiratory gas enters via an alternative route.

There are various different ways in which carbon dioxide can be detected instead of using a colorimetric indicator. For example, the companies NanoMix Inc, Ion Optics Inc, Asthma Alert Ltd and Smart Holograms offer alternative technologies.

The invention could be used with respiratory valves on mechanically-powered resuscitators (such as gas-powered resuscitators) but is not confined to use with respirators and could be used in other applications. Similar detectors could be used to detect for the presence of other gases instead of carbon dioxide.

The invention claimed is:

1. A gas detector used with a gas flow device that supplies respiratory gas to a patient, the gas detector including a gas detector element in a housing arranged to provide a visual indication of change in level of a selected gas, characterized in that the detector is remote from the gas flow device and includes two flexible tubes including a first flexible tube with an opening at one end into the housing for supplying a first gas to the housing from the gas flow device so that the element is exposed to the first gas, and a second flexible tube with an opening at one end into the housing for supplying a second gas to the housing from the gas flow device so that the element is exposed to the second gas, and that the two flexible tubes enable the position of the gas detector housing to be moved relative to the gas flow device and to the patient.

2. A gas detector according to claim 1, characterized in that the gas detector element includes a color change element.

3. A gas detector according to claim 1, characterized in that the gas detector element is responsive to carbon dioxide levels.

4. A gas detector according to claim 1, characterized in that the two tubes extend side-by-side and open into the housing at one end.

5. A gas detector according to claim 1 characterized in that the other end of each of the tubes opens into the gas flow device, wherein the gas flow device comprises a respiratory valve assembly.

6. A gas detector according to claim 1, characterized in that the housing is enclosed and has a transparent portion through which the element can be viewed.

7. A gas detector according to claim 1, characterized in that the housing is arranged to clip onto the gas flow device.

8. A gas detector according to claim 1, characterized in that the housing is arranged for attachment to a respiratory valve assembly.

9. A gas detector according to claim 1, characterized in that housing is disc shape.

10. A respiratory valve assembly including a gas detector according to claim 1.

* * * * *